United States Patent
Bak et al.

(10) Patent No.: US 7,956,260 B2
(45) Date of Patent: Jun. 7, 2011

(54) *GUZMANIA* HYBRID NAMED 'MISTY'

(75) Inventors: Elly Bak, Rijsenhout (NL); Nicolaas D. M. Steur, Oude Niedorp (NL)

(73) Assignee: Corn . Bak B.V., Assendelft (NL)

( * ) Notice: Subject to any disclaimer, the term of this patent is extended or adjusted under 35 U.S.C. 154(b) by 76 days.

(21) Appl. No.: 12/453,370

(22) Filed: May 8, 2009

(65) Prior Publication Data

US 2010/0287659 A1    Nov. 11, 2010

(51) Int. Cl.
*A01H 1/00* (2006.01)
*A01H 5/00* (2006.01)
*A01H 5/10* (2006.01)

(52) U.S. Cl. .......................... 800/323; Plt./371; 800/260

(58) Field of Classification Search ................... Plt./370, Plt./371
See application file for complete search history.

(56) References Cited

OTHER PUBLICATIONS

Print-out of application No. and filing date from Community Plant Variety Office (CPVO) website for corresponding, CPVO application No. 2008/2471 filed Nov. 11, 2008. (http://www.cpvoextranet.cpvo.europa.eu).

*Primary Examiner* — David H Kruse
(74) *Attorney, Agent, or Firm* — Foley & Lardner LLP

(57) ABSTRACT

A new and distinct *Guzmania* hybrid named 'MISTY' characterized by solid growth habit; funnel-form rosette plant, measuring about 42 cm to 46 cm in height (above the pot when flowering); numerous, relatively narrow (measuring about 28 cm to 32 cm in length and about 1.5 cm to 2.5 cm in width color foliage, green in color foliage; superior floral bract production; bracts are greyed-purple in color (closest to RHS 187C); spike inflorescence, measuring about 16 cm in height and about 8 cm to 10 cm in diameter; and long-lasting habit.

5 Claims, 2 Drawing Sheets
(2 of 2 Drawing Sheet(s) Filed in Color)

US 7,956,260 B2

GUZMANIA HYBRID NAMED 'MISTY'

FIELD OF THE INVENTION

The present invention relates to a new, distinct and stable hybrid of *Guzmania* hybrid, hereinafter referred to as 'MISTY'. The present invention relates to seeds which are the *Guzmania* hybrid 'MISTY', as well as, plants and plant parts produced by these seeds which have all of the morphological and physiological characteristics of the *Guzmania* hybrid 'MISTY'. The present invention also relates to methods for producing these seeds and plants of the *Guzmania* hybrid 'MISTY'. Furthermore, the present invention relates to a method of producing progeny *Guzmania* plants by crossing *Guzmania* 'MISTY', as either the female or seed or male or pollen parent, with another *Guzmania* plant and selecting progeny.

BACKGROUND OF THE INVENTION

The present invention relates to a new, distinct and stable hybrid of *Guzmania* hybrid, and hereinafter referred to by the variety denomination 'MISTY'. The new *Guzmania* 'MISTY' originated from a cross made in a controlled breeding program by the inventors in 2001, and then first flowered in 2005, in Assendelft, The Netherlands. The female or seed parent is the *Guzmania dissitiflora* inbred line identified by code 05577108 (unpatented). The male or pollen parent is the *Guzmania kennedii* inbred line identified by code 0557785 (unpatented).

*Guzmania* is a member of the *Bromeliaceae* family. *Guzmania* is predominantly epiphytic with a few terrestrial species and is native to the tropics. For the most part, species vary in diameter from 7 or 8 inches to 3 or 4 feet and have rosettes of glossy, smooth-edged leaves.

Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived.

*Guzmania* may be advantageously grown as pot plants for greenhouse or home use. Typically, the plants are shaded from direct sunlight. During the spring to autumn period, the central vase-like part of the leaf rosette is normally filled with water.

*Guzmania* is native to tropical America. Leaves of *Guzmania* are usually formed as basal rosettes which are stiff and entire and in several vertical ranks. *Guzmania* plants have terminal spikes or panicles which are often bracted with petals united in a tube about as long as the calyx. The ovary is superior and the seeds plumose.

Asexual propagation of *Guzmania* is frequently performed by vegetative means through the use of tissue culture practices. Propagation of *Guzmania* can also be from offshoots which can be detached from the mother plant and grown in an appropriate soil or bark mixture.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

A *Guzmania* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect their morphological and physiological characteristics.

A need exists for a greater variety of *Guzmania* cultivars with attractive ornamental features. Additionally, a need exists for additional *Guzmania* hybrid cultivars that can be easily propagated by seed. The new *Guzmania* 'MISTY' was developed through a controlled breeding program and exhibits unique, desirable and stable characteristics.

SUMMARY OF THE INVENTION

The present invention provides *Guzmania* plant selections that are solid, medium-sized, long-lasting hybrids with superior bract production and red-purple inflorescence that exhibits good keeping quality. The present invention also provides *Guzmania* plant selections with a compound inflorescence with a unique red-purple color which distinguishes the new cultivar from typical *Guzmania*.

These and other objectives have been achieved in accordance with the present invention which provides 'MISTY' as a new *Guzmania* cultivar that is a product of a planned breeding program conducted by the inventors, Elly Bak and Nico D. M. Steur, in Assendelft, The Netherlands, in 2001. The female or seed parent is the *Guzmania dissitiflora* inbred line identified by code 05577108 (unpatented). The male or pollen parent is the *Guzmania kennedyae* inbred line identified by code 0557785 (unpatented).

Both parental cultivars have a sufficient degree of homozygosity such that the progeny of the cross are genetypically and phenotypically uniform. The new hybrid 'MISTY' therefore can be produced by sexual reproduction by crossing the parental inbred lines identified by the codes 05577108 and 0557785 to produce a population of progeny plants, each of which has the combination of characteristics as herein disclosed for the new hybrid 'MISTY'.

Seeds which are the hybrid 'MISTY' are produced by crossing the parental inbred lines identified by the codes 05577108 and 0557785, and are deposited with the American Type Culture Collection, 10801 University Boulevard, Manassas, Va. 20110-2209. ATCC Patent Deposit Designation No. PTA-9855. 2500 seeds were deposited with the ATCC on Feb. 27, 2009.

OBJECTS OF THE INVENTION

The present invention relates to seeds which produce *Guzmania* hybrid 'MISTY'. The present invention also relates to *Guzmania* plants, and parts thereof, having all the physiological and morphological characteristics of *Guzmania* hybrid 'MISTY'. The present invention relates to a plant produced from seeds which are *Guzmania* hybrid 'MISTY'. The present invention also relates to plant parts, such as pollen, seeds or inflorescence produced by *Guzmania* hybrid 'MISTY'.

The present invention relates to a method of producing seed which are *Guzmania* hybrid 'MISTY', comprising the steps of (a) crossing *Guzmania dissitiflora* inbred line identified by code 05577108 (unpatented) as the female or seed parent with *Guzmania kennedii* inbred line identified by code 0557785 (unpatented) as the male or pollen parent; and (b) harvesting seeds produced from said cross.

The present invention also relates to a method of producing plants having all the physiological and morphological characteristics of the *Guzmania* hybrid 'MISTY' comprising the steps of (a) crossing *Guzmania dissitiflora* inbred identified by code 05577108 (unpatented) as a female or seed parent with *Guzmania kennedyae* inbred line identified by code 0557785 (unpatented) as the male or pollen parent; (b) harvesting seeds produced from said cross; and (c) producing plants from said harvested seeds.

The present invention also relates to producing progeny plants from the cross of *Guzmania* hybrid 'MISTY', as the female or male parent, with another *Guzmania* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Guzmania* hybrid 'MISTY' showing the colors as true as is reasonably possible with colored reproductions of this type. Colors in the photographs may differ slightly from the color values cited in the detailed botanical description which accurately describes the color of 'MISTY'.

DETAILED BOTANICAL DESCRIPTION

Figure 1:
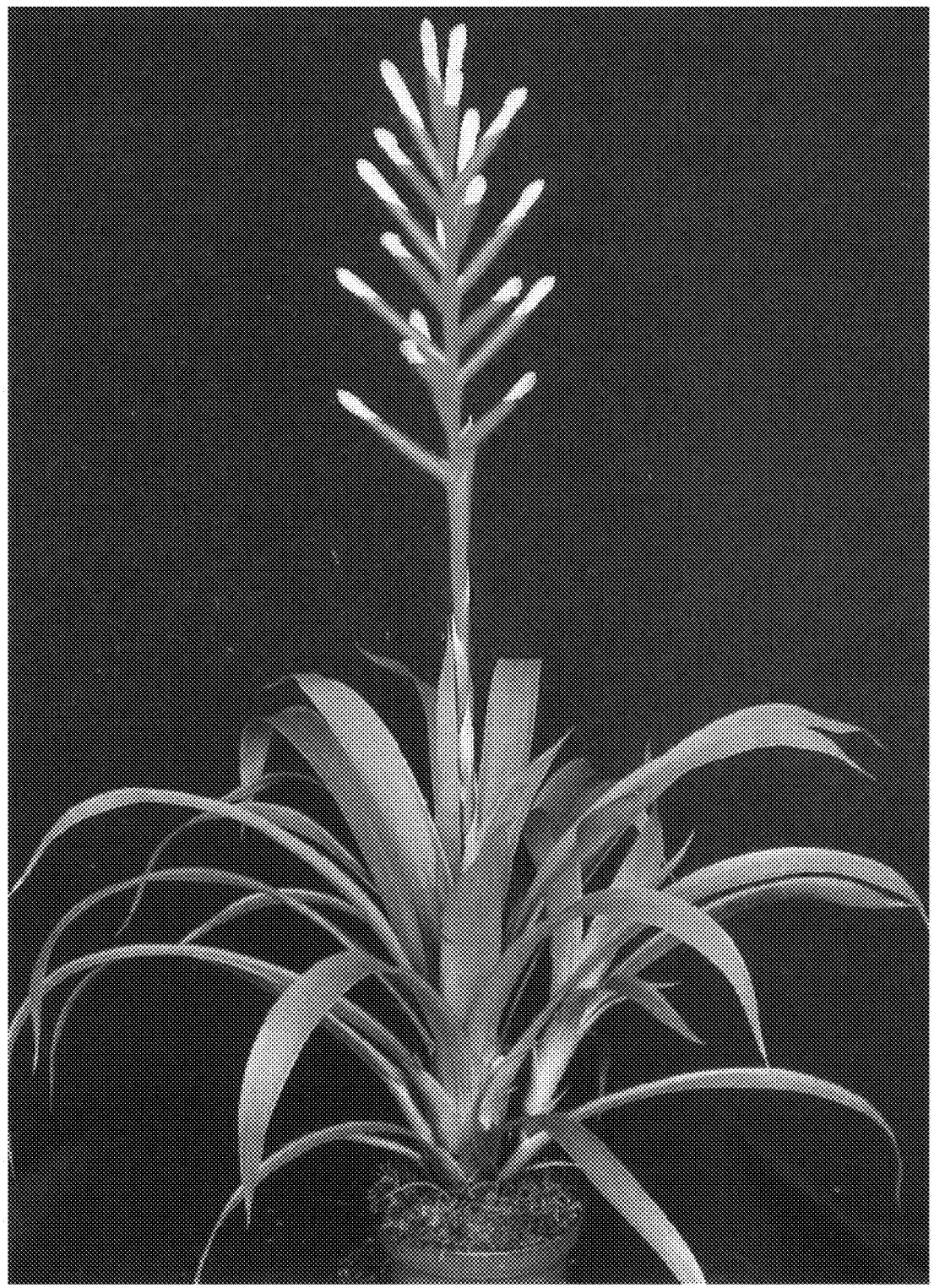
FIG. 1 shows a side view perspective of the primary and top bracts produced by a typical potted, flowering plant of 'MISTY', at 10 months of age from potting.
Figure 2:
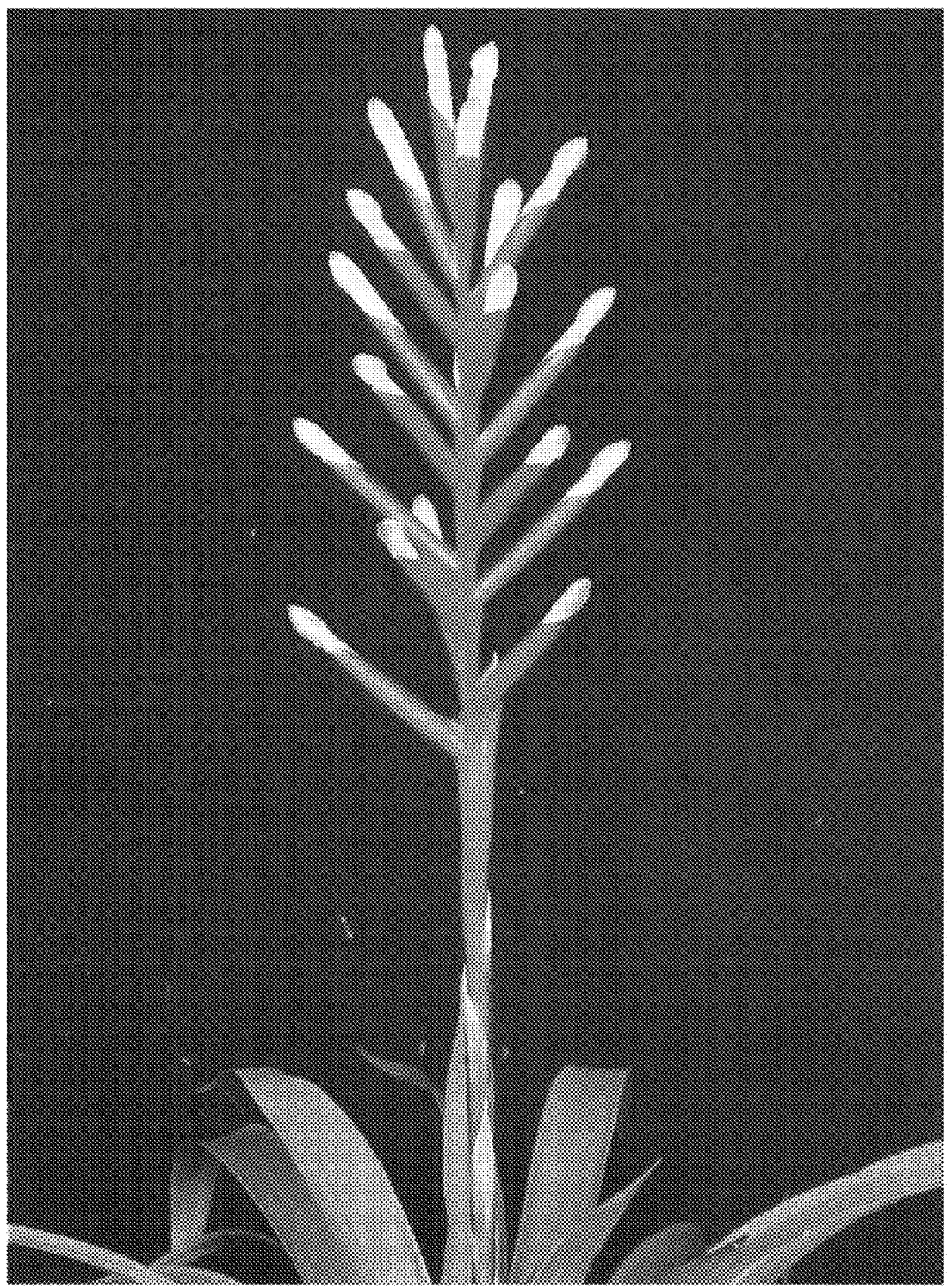
FIG. 2 shows a close-up top view perspective of the inflorescence and top bracts produced by a typical potted, flowering plant of 'MISTY', at 10 months of age from potting.

The present invention was created by the inventors, Elly Bak and Nicolaas D. M. Steur in 2001, and flowered for the first time in 2005 in Assendelft, The Netherlands.

This invention is directed to *Guzmania* plant having all the morphological and physiological characteristics of the hybrid 'MISTY' produced from seeds which are the product of the cross of the *Guzmania dissitiflora* inbred line identified by code 05577108 (unpatented) as the female or seed parent with the *Guzmania kennedyae* inbred line identified by code 055785 (unpatented) as the male or pollen parent. Both parents have a sufficient degree of homozygosity such that the progeny of the cross were, and continue to be, phenotypically uniform. The new hybrid 'MISTY' can therefore be produced by sexual reproduction by crossing of the inbred selections identified by the codes 05577108 and 0557785 to produce a population of progeny plants, each of which has the combination of characteristics herein disclosed for the new hybrid 'MISTY'.

The new hybrid 'MISTY' can also be produced by asexually reproducing progeny from the cross of the parental inbred lines identified by the codes 05577108 and 0557785. Asexual reproduction of the new cultivar by vegetative means by cuttings was first performed in 2005, in Assendelft, The Netherlands. The first 'MISTY' plants propagated through the use of such cuttings flowered in 2006, in Assendelft, The Netherlands, and have demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'MISTY' which in combination distinguish this *Guzmania* as a new and distinct cultivar:

1. Solid growth habit;
2. Funnel-form rosette plant, measuring about 42 cm to 46 cm in height (above the pot when flowering);
3. Numerous, relatively narrow (measuring about 28 cm to 32 cm in length and about 1.5 cm to 2.5 cm in width color foliage, green in color foliage;
4. Superior floral bract production;
5. Bracts are greyed-purple in color (closest to RHS 187C);
6. Spike inflorescence, measuring about 16 cm in height and about 8 cm to 10 cm in diameter; and
7. Long-lasting habit.

Plants of the parental lines, 05577108 and 0557785 (both unpatented) are no longer available to provide a detailed botanical comparison with the new *Guzmania* hybrid 'MISTY'

Of the many commercial cultivars known to the present inventors, the most similar in comparison to the new *Guzmania* hybrid 'MISTY' is the *Guzmania* cultivar 'SPRING' (unpatented). Plants of the new hybrid 'MISTY' differ from plants of 'SPRING' primarily in inflorescence color. Plants of 'MISTY' produce inflorescence which are greyed-purple (closest to RHS 187C) whereas plants of 'SPRING' produce inflorescence which are red (closest to RHS 44A).

'MISTY' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photographs, together with the following observations, measurements and values describe the new *Guzmania* 'MISTY' as grown in a greenhouse in Assendelft, The Netherlands, under conditions which closely approximate those generally used in commercial practice. Plants of 'MISTY' were grown in a greenhouse with day temperatures ranging from 20° C. to 28° C. and night temperatures ranging from 18° C. to 23° C. No artificial lighting or photoperiodic treatments were conducted, but plants of 'MISTY' are forced into flowering. The following fertilizer is added when growing plants of 'MISTY': 1 part nitrogen, 0.6 parts phosphor, 2 parts Kalium and 0.1 parts magnesium.

Color references are made to the Royal Horticultural Society Colour Chart (RHS), 2001 edition, except where general colors of ordinary significance are used. Color values were taken under daylight conditions in a greenhouse in Assendelft, The Netherlands. The age of the plants of 'MISTY' described is about 10 weeks after flowering treatment.

Classification:
Botanical: *Guzmania* sp.
  Parentage:
  Female Parent: *Guzmania dissitiflora* inbred line identified by code 05577108 (unpatented)
  Male Parent: *Guzmania kennedyae* inbred line identified by code 0557785 (unpatented)
  Plant:
  General Appearance and Form:
    Height: About 42 cm to 46 cm (when flowering)
    Width: About 42 cm
    Shape: Funnel form rosette
    Growth habit: Stemless Plant Vigor: Good
Flowering Season: A fully grown plant can flower year round, starting 12 to 13 weeks after induction of natural light or through flowering treatment.
Cold Tolerance: Frost tender. Temperatures below 5° C. may damage plants.
Fragrance: None
Foliage:
Quantity: About 20 (depending on the size of the plant)
Size of Leaf:
   Length: About 28 cm to 32 cm (when flowering)
   Width: About 1.5 to 2.5 cm
Overall Shape: Linear-Lanceolate
Apex Shape: Acuminate
Base Shape: Strap-like around central axis
Margin: Entire
Texture: Smooth
Orientation: Leaf blades arch continuously from base.
Color: Leaf color can vary somewhat depending on growing conditions.
   Immature and Mature:
      Upper surface: Green, RHS 137A
      Under surface: Green, RHS 137C with anthocyanin stripes
Venation: None
Inflorescence:
Borne: Erect stalks
Shape: Spike
Size:
   Length: About 16 cm
   Diameter: About 8 cm to 10 cm
Time of Bloom: A fully grown plant can produce an inflorescence containing about 16 flowers (depending on the size of the plants), and can bloom the whole year starting about 12 to 13 weeks after natural induction or through flowering treatment.
Duration of Bloom: Each flower blooms one (1) day and the total blooming of the whole inflorescence is about three (3) weeks.
Petals:
Number: 3 per flower
Length: About 6.0 cm
Width: About 0.7 cm
Overall Shape: Ligulate
Apex Shape: Obtuse
Base Shape: Fused
Color:
   Upper and under surfaces: Yellow, RHS 7A with green tip, RHS 141B
Sepals:
Number: 3 per flower
Length: About 5.0 cm
Width: About 0.7 cm
Overall Shape: Ligulate
Apex Shape: Acute
Base Shape: Fused
Color:
   Upper and under surfaces: Yellow, RHS 7A with green tip, RHS 141B
Bracts:
Scape Bracts:
Quantity: About 12
Arrangement: Alternate
Size:
Length: About 11 cm (lowest) to about 5 cm (scape bracts positioned just below the primary bracts).
Width: About 1.5 cm to 2.0 cm
Overall shape: Linear-lanceolate, folded around stem
Apex shape: Acuminate
Base shape: Fused
Margin: Entire
Texture: Smooth
Color:
   Upper and under surfaces: Greyed-purple, closes to RHS 187C
Primary Bracts:
Quantity: About 16
Arrangement: Alternate
Size:
   Length: About 5 cm (lowest) to about 2.5 cm (primary bracts become shorter closer to the top of plant)
   Width: About 1.0 cm to 2.0 cm
Overall shape: Linear-lanceolate, folded around stem
Apex shape: Acute
Base shape: Fused
Margin: Entire
Texture: Smooth
Color:
   Upper and under surfaces: Greyed-purple, closest to RHS 187C
Floral bracts: Disposed within the inflorescence.
Reproductive Organs:
Androecium:
   Stamen:
      Number: 6 per flower
      Length: About 5 cm
      Diameter: Less than 1 mm
      Color: Yellow, closest to RHS 8D
   Anther:
      Length: About 0.4 cm
      Color: Green (too small to distinguish RHS value)
   Pollen:
      Amount: Scarce
      Color: Cream (too small to distinguish RHS value)
Gynoecium:
   Pistil:
      Number: 1 per flower
      Length: About 5.8 cm
   Stigma:
      Shape: 3-parted
      Width: About 3.0 mm
      Color: Green, closest to RHS 141B
   Style:
      Length: About 5.0 cm
      Color: Cream (too small to distinguish RHS value)
   Ovary:
      Position: Superior
      Shape: Conical
      Length: About 0.5 cm
      Diameter: About 0.2 cm
      Color: Yellow, closest to RHS 8D
Seeds:
Quantity: About 4000 seeds produced, divided among 16 capsules (depending on the size of the plant). Since new cultivar is a hybrid, seeds produced by new cultivar cannot be used for production.
Shape: Longitudinal
Length: About 0.1 cm
Diameter: Less than 0.1 cm
Texture: Plumose
Color: Brown (too small to distinguish RHS value)
Fruit:
Type: Capsule Quantity: About 16 capsules (depending on the size of the plant)
Shape: Longitudinal
Length: About 2.5 cm
Diameter: About 0.5 cm
Texture: Smooth
Color: Brown, closest to greyed-orange, RHS 165A and RHS 165B
DISEASE/PEST RESISTANCE: No observations made.
DISEASE/PEST SUSCEPTIBILITY: No observations made.

We claim:

1. A *Guzmania* plant named 'MISTY', representative seed having been deposited at the American Type Culture Collection (ATCC) with Patent Deposit Designation No.: PTA-9855.

2. A *Guzmania* seed having American Type Culture Collection (ATCC) Patent Deposit Designation No.: PTA-9855.

3. A plant part obtained from the *Guzmania* plant of claim 1.

4. A method of producing *Guzmania* progeny plant comprising the steps of (a) crossing *Guzmania* 'MISTY', representative seed having been deposited at the American Type Culture Collection (ATCC) with Patent Deposit Designation No.: PTA-9855 as a female or male parent with another *Guzmania* plant, and (b) selecting progeny, 5. The method according to claim 4, wherein the second *Guzmania* plant is 'MISTY'.

* * * * *